United States Patent [19]

Simoneau et al.

[11] Patent Number: 4,564,422

[45] Date of Patent: Jan. 14, 1986

[54] METHOD AND APPARATUS FOR DETECTION OF EROSIVE CAVITATION IN AN AQUEOUS SOLUTION

[75] Inventors: Raynald Simoneau, St-Bruno, Canada; Lucien Chincholle, Verrières le Buisson, France

[73] Assignees: Hydro-Quebec, Montreal, Canada; Centre National de la Recherche Scientifique, Paris, France

[21] Appl. No.: 528,220

[22] Filed: Aug. 31, 1983

[30] Foreign Application Priority Data

Aug. 16, 1983 [CA] Canada .................................. 434664

[51] Int. Cl.$^4$ .......................................... G01N 27/46
[52] U.S. Cl. ..................................... 204/1 T; 204/400
[58] Field of Search ............... 204/404, 1 T, 1 C, 400; 422/53; 324/65 CR; 364/497, 499

[56] References Cited

U.S. PATENT DOCUMENTS

| | | | |
|---|---|---|---|
| 3,486,996 | 12/1969 | Annand | 204/404 |
| 3,766,042 | 10/1973 | Wilson | 204/404 |
| 3,980,542 | 9/1976 | Winslow, Jr. et al. | 204/412 X |
| 3,996,124 | 12/1976 | Eaton et al. | 204/412 X |
| 4,056,445 | 11/1977 | Gauntt et al. | 204/404 X |
| 4,065,373 | 12/1977 | Martin et al. | 204/412 X |
| 4,087,742 | 5/1978 | Khoo | 204/404 X |
| 4,147,596 | 4/1979 | Baboian et al. | 204/404 X |
| 4,221,651 | 9/1980 | Mansfeld et al. | 204/412 |
| 4,395,318 | 7/1983 | Tait et al. | 204/404 |

FOREIGN PATENT DOCUMENTS 2421378 10/1979 France .

OTHER PUBLICATIONS

Eaton et al., "A Flushed Mounted Probe for Instantaneous Corrosion Measurements in Gas Transmission Lines", N.A.C.E., 6/1978.

"Modern Electrical Methods for Determining Corrosion Rates", N.A.C.E., 1970.

Paper entitled, "L'Effet d'Activation Andodique de la Cavitation Erosive", presented at IAHR Symposium, Sep. 19, 1982.

"Liquid-Erosion Failures", ASM Metals Handbook, vol. 10, 1975.

*Primary Examiner*—G. L. Kaplan
*Assistant Examiner*—Nam X. Nguyen
*Attorney, Agent, or Firm*—Schwartz, Jeffery, Schwaab, Mack, Blumenthal & Evans

[57] ABSTRACT

Method and device for quantitatively measuring the intensity of erosive cavitation present in an aqueous solution such as, for instance, fresh water. According to the method, a set of measuring electrodes is placed in the liquid, these electrodes including a reference electrode, at least one auxiliary electrode and at least one working electrode made of a metal selected from those capable of forming highly insulating oxide films capable of becoming thicker by ionic mobility under the action of an electric field, this metal being preferably titanium. The auxiliary and working electrodes are located in the zone where it is desired to measure the cavitation and a constant anodic voltage is applied across the working electrode by means of the auxiliary and reference electrodes. The intensity of the anodic current is then measured and any variation in the intensity of this current is detected and measured. The variation thus measured is, in terms of the appropriately selected constant anodic voltage applied, directly proportional to the intensity of erosive cavitation in the measure zone. This method as well as the device for carrying it out may particularly be useful in the design of hydraulic machines; during the testing of models or prototypes such as during tests on pumps, turbines, propellers or water valves, as well as for the supervision of machines in operation in hydraulic, thermo or nuclear plants, or in pumping stations for fresh or salt water.

26 Claims, 14 Drawing Figures

METHOD AND APPARATUS FOR DETECTION OF EROSIVE CAVITATION IN AN AQUEOUS SOLUTION

The present invention relates to a method as well as to a device for quantitatively measuring the intensity or erosive cavitation present in a liquid, namely soft water.

The cavitation phenomenon to which hydraulic machines such as turbines, pumps, propellers, valves or exchangers, are subjected, is a problem well known to specialists. By cavitation phenomenon it is to be understood the phenomenon whereby a cavity or a vapor bubble develops in a liquid when the local pressure falls below the vapor pressure. When the pressure rises again above that of the vapor, the gas or vapor bubble abruptly collapses. This implosion is accompanied by powerful physical phenomena, namely by a microjet which follows the bubble and the speed of which may reach several hundreds of meters per second.

When such a microjet meets a wall, its kinetic energy is changed into a localized shock wave capable of deforming the the hardest metallic surface and thus produce an important mechanical erosion. The intensity of the localized stresses produced by such impulses may spread over a very wide range depending on the natural conditions of the liquid, of the temperature and of the presence of foreign gases, of the rate in the pressure variation and of the liquid flow speed. These repeated shocks erode the metallic surface by propagating fatigue fissures (elastic deformation) or by plastic deformation leading to stripping of particles of small dimension.

The implosion of cavitation bubbles further produces localized high speed water displacement, generation and displacements of gases such as oxygen and hydrogen or yet electric charges.

As indicated above, the drawbacks associated with cavitation which, if the cavitation is not well controlled, may lead to a more or less fast degradation of any type of hydraulic equipment and the difficulties met to detect it are well known to specialists.

Methods and devices for detecting cavitation by measuring the noises which generally accompany this phenomenon have already been proposed. The use of these methods and devices is however complex and tricky, and further present very great drawbacks such as providing only a general information which is not localized and from a relatively high threshold in a noisy installation. Furthermore, they cannot indicate whether or not the cavitation detected is of the erosive type.

One of the two inventors of the present application, Mr. Chincholle, has also proposed, several years ago, a method as well as a device using the measure of the variation of the electrochemical potential produced by the erosion of a passivated metallic surface dipped into a cavitating liquid to detect the presence of an erosive cavitation. This invention has been the object of French Pat. No. 78-09255 of Mar. 30, 1978, which patent has been published under No. 2,421,378. It presents several interesting aspects of which most important is, without doubt, the fact that it makes it possible to convert the presence of an erosive cavitation into an electric signal, which makes it particularly well adapted to automatic regulation chains of a hydraulic installation. The device described in this French patent has, however, the drawback that it is difficult to calibrate because, on the one hand, the ranges of cavitation intensity met in hydraulic machines are quite wide and difficult to reproduce in laboratory and, on the other hand, the measured electric voltage which appears to be proportional to the rate of deactivation of the surface of the working electrode, is in fact proportional to the rate of erosion, that is to the loss of weight of the surface of the electrode, only within a certain range of average cavitation intensity.

It is an object of the present invention to provide a method as well as an electrochemical device capable of avoiding the aforesaid drawback mentioned with respect to the process and the device disclosed in French patent published under No. 2,421,378.

More specifically, the object of the present invention is a method as well as a device of the electrochemical type for measuring the activity of erosive cavitation present in an aqueous liquid, namely soft or salted water, the measurement being quantitative, localized, instaneous and continuous.

The present invention is based on the discovery made by one of the inventors that there exists a relation of direct proportionality between the erosive cavitation in water, represented by the rate of erosion in the water, and the value of the anodic current measured on one working electrode made of a material selected from those capable of forming a highly insulating oxide film which becomes thicker by ionic mobility under the action of an electric field.

As broadly claimed herein, the invention is a method of quantitatively measuring the intensity of erosive cavitation present in a liquid, the method comprising:

mounting, in said liquid, a set of measuring electrodes comprising a reference electrode, at least one auxiliary electrode, and at least one working electrode made of a metal selected from metals capable of forming highly insulating oxide films becoming thicker by ionic mobility under the action of an electric field, the said working electrode being located in a zone where cavitation is to be measured;

applying a constant anodic voltage across said working electrode by means of said auxiliary and reference electrodes;

measuring the intensity of the anodic current, and detecting and measuring any variation in the said intensity of the current, each variation thus measured being directly related to the intensity of erosive cavitation in the said zone.

The invention is also broadly claimed herein as a device for quantitatively measuring the intensity of erosive cavitation present in a liquid, the device comprising:

a set of measuring electrodes mounted in the said liquid and comprising a reference electrode, at least one auxiliary electrode, and at least one working electrode made of a metal selected from those capable of forming highly insulating oxide films becoming thicker by ionic mobility under the action of an electric field, the said working electrode being located in a zone or zones where cavitation is to be measured;

means to apply a constant anodic voltage across each working electrode by means of said auxiliary and reference electrodes, and means to measure the intensity of the anodic current and to detect and measure any variation in the intensity of the said current, each variation thus measured being directly related to the intensity of erosive cavitation in the measure zone.

Among the metals having the above-mentioned criteria, may be mentioned aluminum, magnesium, niobium, tantalum, titanium and zirconium.

According to a preferred embodiment of the invention applied to the quantitative measurement of the activity of erosive cavitation in water, the working electrode is advantageously made of titanium preferably so selected that it has the lowest hardness possible, and the constant anodic voltage applied across the working electrode is of the order of 0.5 V measured with respect to a reference electrode made of saturated calomel (SCE). Under this applied voltage, it has indeed been possible to determine a relationship of direct proportionality between the intensity of the anodic current and the erosion rate and this in more than three order of magnitude from 0.05 to 100 mm per year. It has also been possible to establish that this proportionality varies very little with temperature, the calibration being the same at 25° and 40° C. although slightly greater at 6° C.

The device according to the invention is of particular interest in that it may easily be adapted to allow simultaneous measurements at various different locations with the assistance of several separate conditioning means. The latter may include a high impedance multiple potentiostat to fix the desired anodic voltage for each of the working electrodes of the device, as well as multiscale calibrated resistance galvanometer for measuring the intensity of the inodic current. The signals provided by the probes may be read in sequence by means of a multiplexer controlled by a microcomputer or microprocessor. For more accuracy, a digital voltmeter with integrator may be used.

The method as well as the device according to the invention may advantageously be used in the design of pumps, turbines, propellers or valves, for the evaluation of the performance of prototypes, for the supervision of hydraulic, thermo or nuclear machines, soft or salt water pumping stations or for any other type of research and development implicating a cavitation phenomenon.

This method as well as the device are particularly advantageous due to the fact that they provide, in a relatively simple manner, a quantitative measure of the intensity of erosive cavitation and this, in a localized, instantaneous, continuous manner and with far more sensitivity than with any other known method. The device according to the invention further has the advantage of being almost unusual because of the appropriate selection of material used for making the working electrodes.

The invention as well as its various other advantages will appear more clearly in the detailed and non-limitative description that follows made in reference to the appended drawings.

Figure 1:
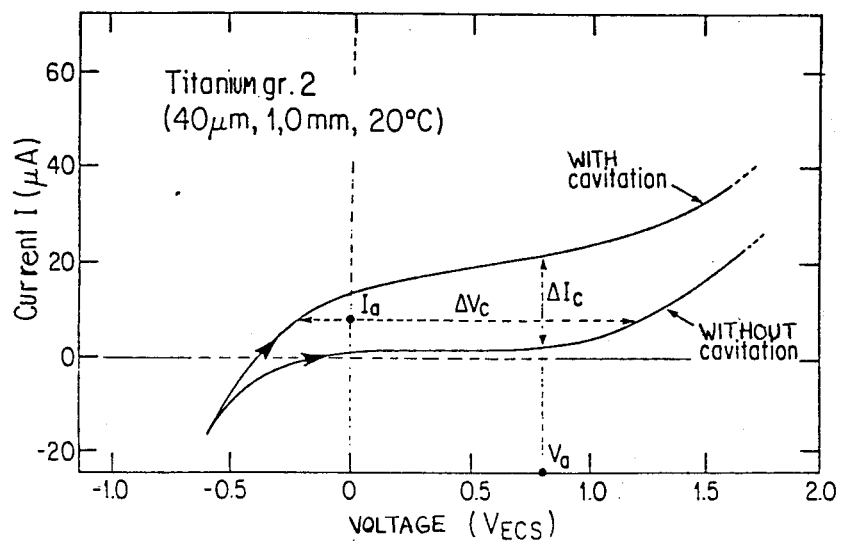
FIG. 1 is a curve illustrating the anodic activation of titanium.

As previously indicated, the present invention is based upon the discovery made by one of the inventors that there exists a relation of direct proportionality between the strength of the anodic current that may be determined by means of a working electrode made of a metal of a well-defined type across which is applied a constant anodic voltage, and the erosion rate corresponding to the erosive cavitation intensity taking place in a liquid in which the working electrode is dipped.

According to the invention, the metals of well-defined type useable for the manufacture of working electrodes ensuring the existence of the aforementioned proportionality relation, are the metals known under the name "valve" metals. These metals have, by their electronic configuration, the common property of forming highly insulating oxide films rendered thicker in an electric field by ionic mobility. The metals having this common feature are aluminum, magnesium and more generally all metals of the groups IVB and VB of the periodic table, including namely titanium, niobium, zirconium and tantalum.

For a better understanding of the selection to be made of this particular type of metals, reference should be made to the research works carried out by the inventors and of which the results are given in a communication entitled "L'effet d'activation anodique de la cavitation érosive" during international symposium organized at Amsterdam in September 1982 under the sponsorship of the International Association for Hydraulic Research (IAHR). The results thus given have made it possible to observe that, on the one hand, erosive cavitation causes a drop in anodic voltage in galvano-static conditions and an increase in anodic current in potentio-static conditions and that, on the other hand, these drops of anodic voltage and increases of anodic current are related to an anodic activation phenomenon (also known as depassivation), according to which erosion due to cavitation comes to destroy the oxide film which tends to spontaneously rebuild itself at the surface of the working electrode. This reconstruction of the passivation film, permanently destroyed at the surface of the electrode, changes the electrochemical potential of the metal of which the electrode is made by rendering it less noble and less positive. This then implies the flow of an anodic current which proves to be proportional to the quantity of repassivation charge necessary to reconstitute a unit of volume of the oxide film multiplied by the total volume of oxide to be reconstituted.

It is therefore quite obvious that the above-mentioned metals of which the oxide films are highly insulating and, thence, allow the creation of an electric field favorable to the ionic diffusion and the growth of the oxide film under anodic polarization, are the metals which show the highest activation anodic current.

On the contrary, the metals such as cobalt, chromium and stainless steels which form very thin protective oxide films show relatively weak activation currents in the presence of a cavitation phenomenon.

The following tables clearly illustrate this experimental verification made by the inventors.

tion during the action of cavitative erosion produces very high anodic activation currents.

The existence of the anodic activation phenomenon, of which reference has just been made, comes out clearly from the polarization curve illustrated in FIG. 1 of the drawings, which curve has been obtained from measurements carried out on a working electrode made of grade 2 titanium (99% Ti; 0.03% $N_2$; 0.10% C; 0.3% Fe and 0.25% $O_2$ by weight). These measurements were made in the same experimental conditions as previously mentioned, except for a gap of 1 mm rather than the 0.5 mm mentioned above.

As this curve shows, the anodic activation phenomenon may be studied either by observing the variations in the anodic current when the anodic voltage is maintained constant (potentio-static measurement), or by measuring the changes in the anodic voltage when the current is maintained constant (galvano-static measurement). In the first case, the cavitation produces an increase in the anodic current $\Delta Ic$, whereas in the other case, the cavitation produces a drop in the anodic voltage $\Delta Vc$.

As previously indicated, the measurement of the in-

|  | Brinell hardness | No-load Potential $E_a(I = O)$ ($V_{SCE}$) | $E_a(I = 25 \mu A)$ ($V_{SCE}$) | Field of passivation $\Delta E = E_a(25 \mu A) - E_a(O \mu A)$ (V) | Applied voltage $E_a(V_{SCE})$ | Activation current $\Delta I_c(\mu A)$ |
|---|---|---|---|---|---|---|
| Ti gr. 2 | 120 | −0.05 | 1.35 | 1.4 | 0.3 | 50 |
| Ti gr. 4 | 160 | −0.05 | 1.45 | 1.5 | 0.3 | 25 |
| Al 59 | 18 | −0.5 | −0.30 | 0.20 | −0.6 | 280 |
| Al 6061 | 90 | −0.4 | −0.35 | 0.75 | −0.6 | 120 |
| Ni 39 | 180 | 0.0 | 0.8 | 0.8 | 0.3 | 45 |
| Co 49 | 85 | −0.45 | — | 0 | −0.5 | 8 |
| Cr |  | −0.1 | 0.63 | 0.73 | 0.4 | 5 |
| Nb 39 | 60 | −0.15 | 0.85 | 1.0 | 0.3 | 50 |
| Zr 39 | 135 | −0.1 | 1.6 | 1.7 | 0.3 | 35 |
| Steel 304 | 150 | −0.04 | 1.1 | 1.04 | 0.6 | 8 |
| Steel 316 | 150 | −0.05 | 1.1 | 1.05 | 1.0 | 5 |
| Steel 1020 | 150 | −0.31 | — | 0 | 0.0 | −120 |
| Stellite 21 | 240 | −0.04 | 0.72 | .76 | 0.4 | 3 |
| Ta | 90 | −1.0 | 2.5 | 3.5 | 2.0 | 25 |
| Mg | 31 | −1.5 | 1.4 | 0.1 | −2.0 | 90 |

In this table are given the field of passivation (arbitrarily defined as the zone where the anodic current is lower than 25 μA) as well as the intensity of the activation current ΔIc expressed in μA in terms of an applied voltage $E_a$ measured with respect to a saturated calomel electrode in similar experimental conditions, to wit:
apparatus: ultrasonic cavitation bench;
vibration amplitude: 40 μm peak to peak;
gap between the tip of the vibrating cone and the test piece: 0.5 mm; and
experimental liquid: tops water at 20° C.

As this table clearly brings out, certain metals such as cobalt or carbon steel 1020 have passivation fields that are almost inexistent. Other metals such as aluminum and magnesium have very narrow passivation fields although they do have relatively high activation current. Other metals such as stainless steels 304 and 316, niobium, titanium, zirconium and tantalum show very wide passivation fields and thus a very stable behavior in water. Finally, other metals such as aluminum, magnesium, titanium, niobium, zirconium and tantalum show important activation currents under applied voltage which, as earlier indicated, is easily explained by the fact that these metals have the common feature of forming relatively thick oxide films of which the reconstitutensity in erosive cavitation according to the invention is advantageously carried out in potentiostatic mode. It has indeed been established that there exists a relation of direct proportionality between the rate of erosion measured by loss of weight and the intensity of the activation current measured in the particular case where the working electrodes used are made in one of the aforementioned valve metals which show a relatively stable behavior in water and important activation currents under applied voltage.

Figure 2:
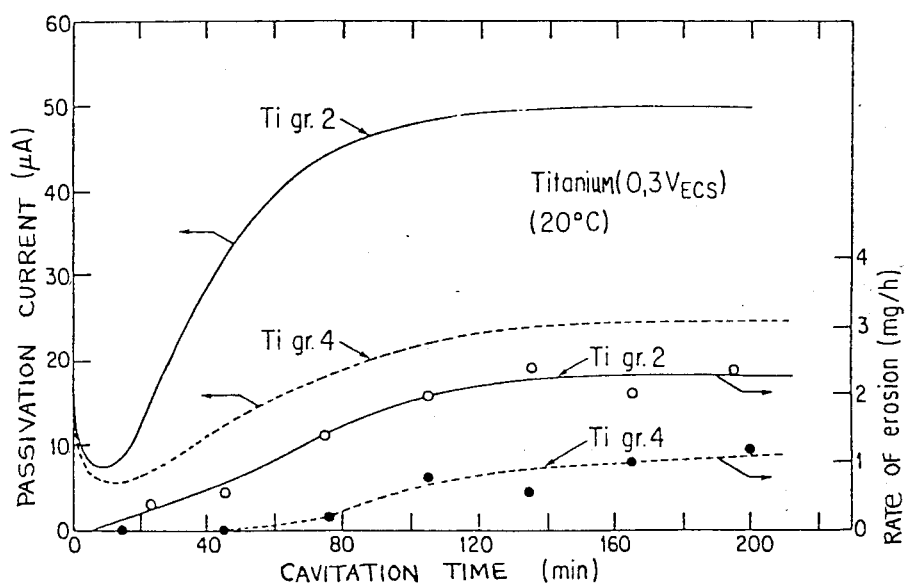
FIG. 2 is a curve simultaneously providing, with respect to time, the intensity of the activation current and the rate of erosion of two electrodes made of two types of titanium.

The existence of this relation of proportionality clearly appears from the curve shown in FIG. 2 which gives, in unbroken lines, the intensity of the activation current of two electrodes made of two types of titanium in terms of time, and, in broken lines, the rate of erosion of these two same electrodes during the same period of time. As is shown in a simple comparison of the intensity and the rates obtained in the case of both electrodes after a certain period of time necessary for the stabilization of the cavitation phenomenon (incubation period), there exists a direct relation of proportionality between the rates of erosion measured as weight (expressed in milligrammes per hour) and the intensities of activation current (expressed in microamperes), which are twice smaller for the grade 4 titanium (98,5% Ti; 0.05% $N_2$;

0.10% C; 0.5% Fe and 0.40% O₂ by weight), harder and more resistant than grade 2 titanium.

Figure 3:
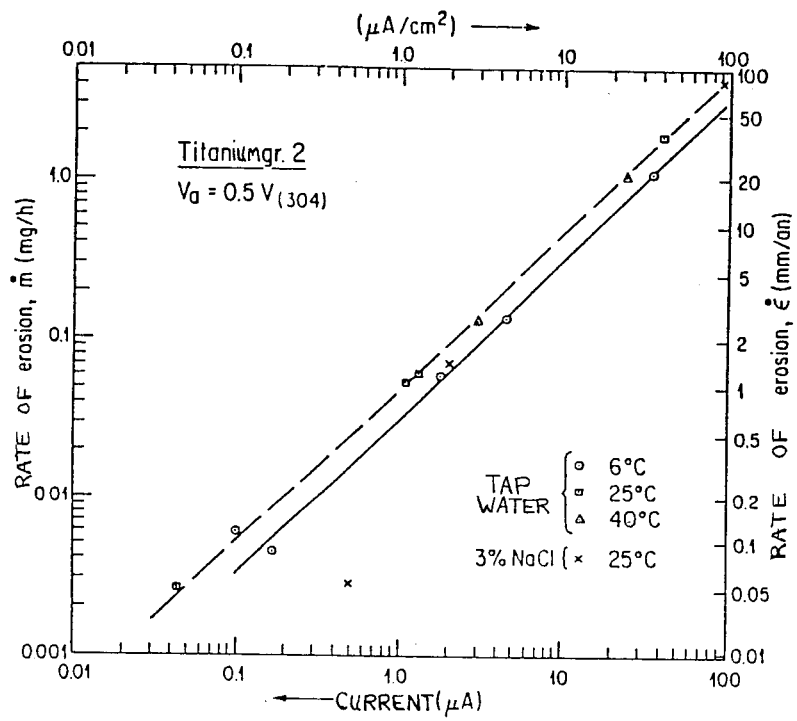
FIG. 3 is a curve for the calibration of a probe made of grade 2 titanium in soft domestic water or salt water giving the rate of erosion as a function of the intesity of the anodic current.

The existence of this relation of direct proportionality likewise appears from the calibration curve illustrated in FIG. 3 of the drawings, giving the rate of erosion of a working electrode made of grade 2 titanium in terms of the strength of the anodic current measured in soft water at 6°, 25°, and 40° C. as well as salt water by addition of 3% of sodium chloride at 25° C. As this curve shows, there exists a relation of direct proportionality between the strength of the anodic current and the rate of erosion in more than 3 orders of magnitude (from 0.05 to 100 mm per year). This curve likewise shows that the calibration varies very little with temperature. This calibration is the same at 25° and 40° C. However, at 6° C., the response in current shows to be somewhat higher. Nevertheless, in both cases, the current and the rate of erosion are tied by a linear relation, the slope of the line obtained on the log—log graph is indeed equal to 1. This comes to confirm the exactitude of the mathematical model suggested in the communication submitted at Amsterdam in September 1982 during the IAHR symposium mentioned previously, to wit that there exists a relationship of the type:

$$\frac{i}{s} = k\epsilon$$

wherein:
i is the intensity of the current (expressed in $\mu A$);
s is the area of the eroded surface (expressed in $cm^2$);
k is a constant; and
$\epsilon$ is the rate of erosion (in mm per year).

Figure 8:
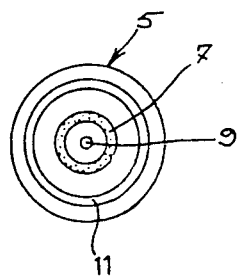
FIG. 8 is a plan view of the exposed surface of one of the probes provided downstream on the ejector pump illustrated in FIG. 6.

In the case illustrated in FIG. 8:
k=1.12 at 25° and 40°
k=1.56 at 6° C.

One tentative explanation for the difference in the measured constant for different temperatures is that the specific passivation charges are greater at low temperature.

As this curve finally shows, the relation shows not to be linear in salt water at 25° C. for the full range of cavitation intensities, as if the passivation charges were then larger or the eroded particles smaller at low erosion rates.

Figure 4:
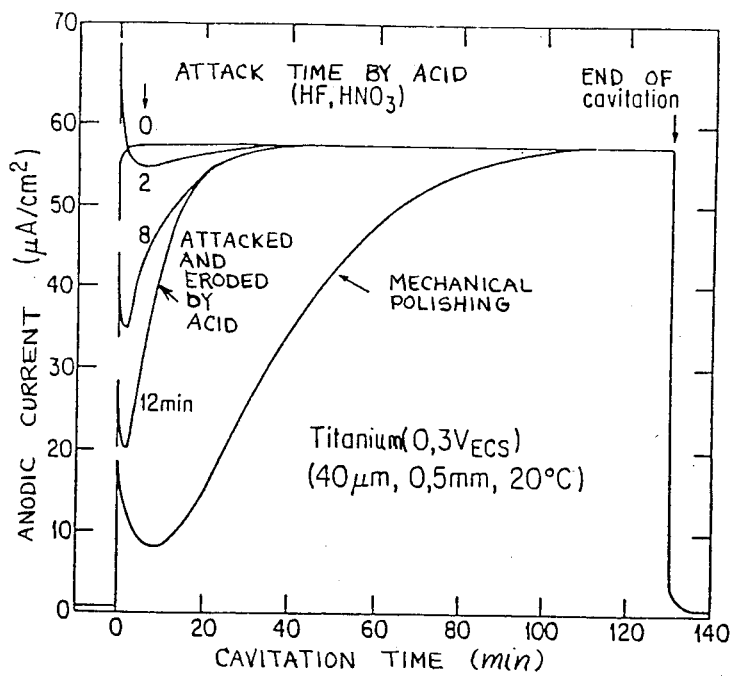
FIG. 4 is a curve giving the strength of the anodic activation current with respect to the time of cavitation in the case of a titanium electrode as affected by superficial acid dissolution.

This curve thus clearly shows that the potentio-static situation for measuring the activity of erosive cavitation offers excellent stability, reproducibility and proportionality. This verification, particularly with respect to the stability and the reproducibility of the measurements, is that much more accurate that tests carried out in laboratory have clearly shown that the surface treatments to which the working electrode was subjected were affecting the calibration only during the noted incubation period, as can be verified from the curve shown in FIG. 4 which gives the strength of the anodic current measured as a function of cavitation time for one titanium electrode in the same operating conditions, after having successively subjected the surface of the electrode in question to different surface treatment such as an attack by acid during a more or less extended period of time or a strong mechanical polishing. The results obtained show that only the initial incubation period varies, the maximum activity obtained being identical each time as soon as the electrochemical phenomenon connected to cavitations is stabilized. Besides, this curve shows that an attack by acid, removing a superficial layer of 20 microns or more from the surface of a previously incubated or eroded titanium sample, causes complete reappearance of the incubation period. The latter is thus related to the mechanical incubation by deformation, work-hardening, fatigue or cracking of a fine superficial layer of the metal which increases the rate of erosion until a permanent state is reached.

Figure 5:
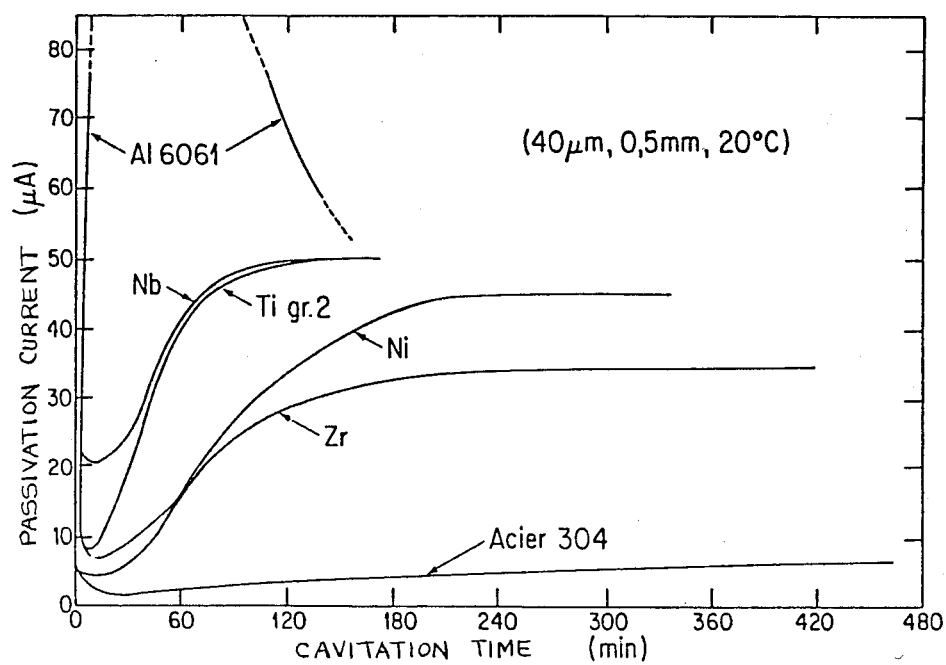
FIG. 5 is a curve giving the intensity of the anodic activation current for several passive metals, as a function of time.

The incubation period of the various metals that can be used in making the working electrodes according to the invention depends of course on the nature of the metal and, more precisely, its hardness. The curve shown in FIG. 5 gives the strength of the anodic current measured in terms of cavitation time for working electrodes made of a 6061 aluminum alloy, of niobium, of grade 2 titanium, of nickel, of zirconium and of type 304 stainless steel. This curve clearly shows that these incubation periods vary widely, going from a few minutes for aluminum to several hours in the case of a non-valve metal such as stainless steel. The similar curve illustrated in FIG. 1 also shows a faster increase in current and consequently a shorter incubation period in the case of grade 2 titanium, that is in the case of the softest titanium. According to the invention, it is thus preferable to use, for the same type of valve-metal used, that one which has the lowest possible hardness.

From the curve illustrated in FIG. 1, it could be thought that aluminum, 99.999% pure, which aluminum is very soft, could be the most interesting valve metal for measuring the smallest erosion rates, since this metal shows that it has a very small resistance to cavitation. Nevertheless, tests have shown that pure aluminum has too narrow a passivation field in domestic water to be truly of interest from an industrial point of view. Furthermore, it has been observed that the stability of its oxide film and consequently its electrochemical equilibrim changed with time after passivation. It has particularly been verified that a passivating oxide film freshly formed on the surface of a pure electrode is very weak and has very little protective value, the flow of water without cavitation being sufficient to remove it. For this reason, this particular material shows to be of little interest for the manufacture of working electrodes for the direct and continuous measurement of cavitation intensity in components dipped in water. This drawback may however become an advantage to the extent where, the degree of depassivation and of reactivation of the aluminum oxide film being directly proportional to the speed of water on the surface; this metal could be used for the making of a flow meter.

Tests carried out by the inventors have shown that the metal which proves to be of most interest according to the invention is titanium. Indeed, this metal, further to being one of the valve metals having very strong anodic currents and having a good stability in currently used waters, has the advantage of being a well-known material with properties that are defined in ASTM standards and of being reproducible. Furthermore, it is sometimes utilized in hydraulic machines where its use as structural material would give a direct measure of the wearing rates of the components. Finally, this material is of particular interest to the extent where it may easily be used to make electrodes having a wide surface, because of its very good passivation and because of the negligible current that exists over its non-eroded surfaces.

To improve the detection limit of titanium, it has been tried to make it less resistant by subjecting it to hydrogen thermal treatments suited to make it more brittle or harder. These attempts have however proven to be unsuccessful although, as indicated previously, the best results have in all evidence been obtained with the softest titanium possible.

Tests carried out by the inventors have shown that the detection limit of titanium for very weak activity in potentio-static conditions is optimized by adjusting the applied anodic voltage at +0.5 volt SCE. Other tests have made it possible to show that a titanium electrode, because of its very good passivation, makes it possible to detect an erosion located only on a small proportion of its surface, the proportion which is not activated by erosion giving only a negligible anodic current. This last observation may prove interesting to allow a fine localization on a wide probe surface, by simply taking care to initially tint the surface of titanium by anodization, this being possible even in operation, the zone subjected to erosive cavitation being then revealed by a change in color. Because of this technique, it is thus possible to detect, quantify and localize any erosion that may take place inside a hydraulic equipment made of titanium.

All of the results mentioned above therefore clearly show that it is possible easily to measure quantitatively the intensity of erosive cavitation appearing in water by mounting in the water a set of measuring electrodes comprising a reference electrode which may, for instance, be a calomel saturated electrode, or a stable passive metal electrode (stainless steel, titanium), at least one auxiliary electrode and at least one working electrode made of one of the valve metals mentioned above. The auxiliary and working electrodes may advantageously be grouped together to form a compact probe comprising a core body made of an insulating material such as an epoxy resin in which are embedded, on the one hand, the working electrode, the latter having cylindrical shape suitable to present an annular exposed surface and, on the other hand, the auxiliary electrode constituted by a mere stainless steel rod of the 316 type positioned at the center of the core body and of the working electrode. This probe has obviously to be localized in the zone where the cavitation measurement is to be taken.

It is then sufficient to apply a constant anodic voltage across the working electrode by means of the auxiliary and reference electrodes, to measure the strength of the anodic current then to detect and measure any variation in the said current strength in order to measure the activity of cavitation in the selected zone, each variation thus measured being indeed directly related to the activity of erosive cavitation in the measure zone.

It is appropriate of course during the measurements to take the initial incubation period into account, unless there has been an initial preparation and conditioning, in order to obtain the best reproducible signal with the best resolution.

In order to carry out the above-described method, it is sufficient to use a set of measuring electrodes disposed in the liquid, this set of electrodes comprising a reference electrode and a set of probes each comprising an auxiliary electrode and a working electrode made in one of the valve metals mentioned above. It is of course necessary to use suitable means to apply a constant anodic voltage across each working electrode by means of the auxiliary and reference electrodes, and means to measure the intensity of the anodic current in order to detect and measure any variation in the current intensity.

Figure 14:
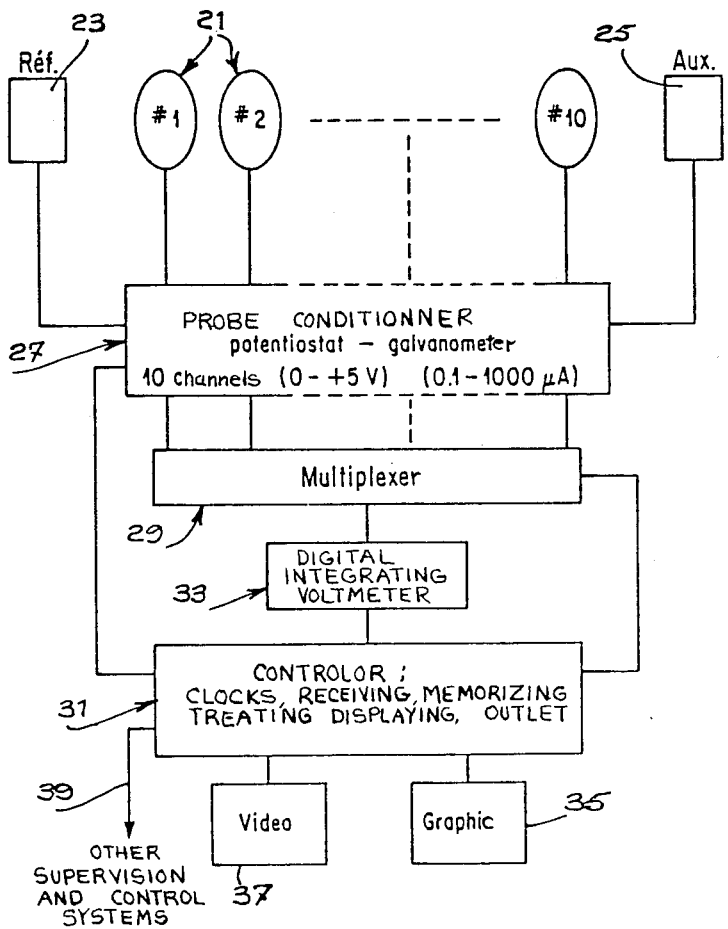
FIG. 14 is a block diagram of a complete device according to the invention for the measurement of the intensity of erosive cavitation in a hydraulic machine.

FIG. 14 schematically illustrates a complete device made according to the invention to measure quantitatively the intensity of erosive cavitation present in a liquid. This device is conceived to allow simultaneous measurement of the activity of erosive cavitation at several different points in a hydraulic machine (not illustrated) by means of several working electrodes 21 (10 in number, for instance).

Of course, in order that this measurement be made possible, it is necessary that each working electrode 21 be separately "conditioned" by the application of an anodic potential by means of an auxiliary electrode 23 and a reference electrode 25. One of these two electrodes may, in practice, be constituted by the hydraulic machine as a whole whereas the other as well as each working electrode must be electrically insulated from the machine by means of an epoxy resine or any other suitable insulating material.

On this point, it is proper to mention that it may be advantageous to use, as reference electrode 23, an electrode of the same nature and of the same shape as the working electrodes 21, taking care to locate this reference electrode in a place where the flow of liquid does not create any cavitation.

Besides electrodes 21, 23 and 25, the device comprises a conditioner 27 including a high-impedance multiple potentiostat to apply a constant anodic voltage across each working electrode by means of the auxiliary and reference electrodes, as well as a multiscale calibrated resistance galvanometer (from 0.1 $\mu$A to 1000 $\mu$A), to measure the strength of the anodic current and thus detect and measure any variation in the strength of the measured current for each of the working electrodes 21.

The signals provided by the working electrodes 21 are read in sequence by means of a multiplexer 29 controlled by a programmable control device 31 that may be a microcomputer or microprocessor including a clock to adjust the frequency and the duration of the readings. To obtain a maximum of accuracy, a digital integrating voltmeter 33 may be arranged between the multiplexer 29 and the device 31 for treating the signals transmitted from one to the other.

The programmable electronic control device 31 may advantageously be provided with means for receiving and memorizing the measurements provided by each probe. These means may be constituted by a memory unit such as a disc, for example. The device may additionally include means for treating the signals thus memorized in such a way as to convert them directly into erosion rate units, accumulated metal losses, depth of penetration, or in operating period before the following repair. Besides, the programmable electronic device 31 may have means to display the results obtained in analogue or digital form by continuous display in real time by graphic illustration 35 or video illustration 37.

Finally, the programmable electronic device 31 may have a digital outlet 39 in view of an interface with a complete supervision or control system for the hydraulic machine.

EXAMPLE 1

A test has been carried out on an ejector pump by using a basic device such as that described above.

Figure 6:
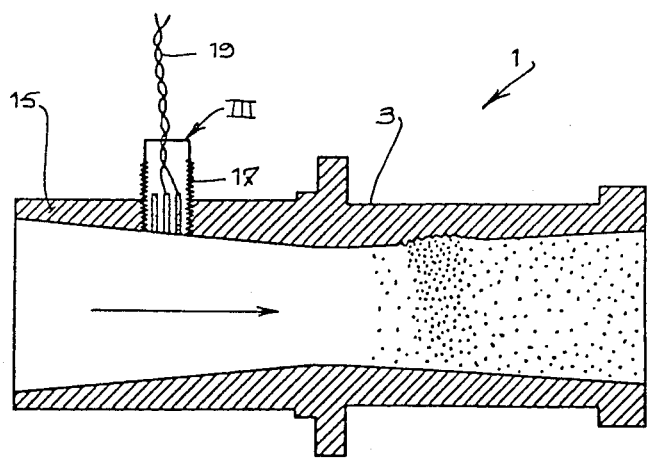
FIG. 6 is a schematic; and longitudinal cross-sectional view of an ejector pump on which titanium probes have been mounted for testing purposes.
Figure 7:
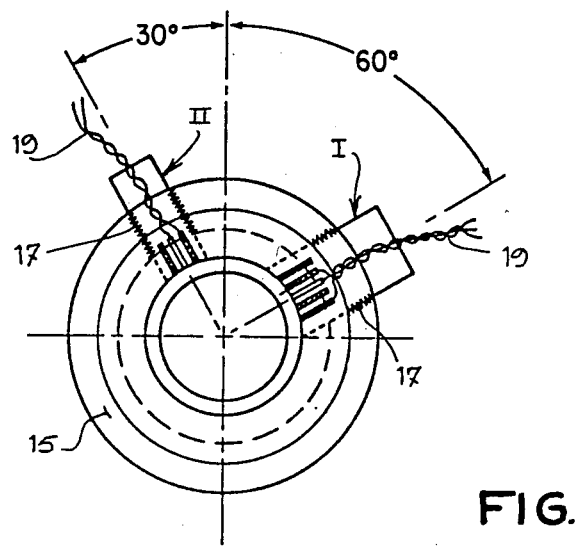
FIG. 7 is a transverse cross-sectional view across the downstream part of the ejector pump illustrated in FIG. 6, showing the positioning of two titanium probes.

The Venturi tube of the pump on which this test has been made is schematically illustrated on FIGS. 6 and 7. This pump used upstream water at high pressure (240 m head) to pump a greater volume of downstream water for cooling purposes.

The inside of the Venturi tube 1 of the pump was made of type 316 stainless steel and showed localized wear due to erosive cavitation varying between 0.1 and 1 mm per year at the worst spots.

Three annular probes of 0.8 cm$^2$ in cross-section have been installed on this pump to measure the instantaneous rate of erosion. The first two of these probes, respectively numbered I and II have been installed in the area of maximum erosive cavitation activity (downstream of the throat 3 of the Ventiru). The third one of these probes, numbered III, has on the other hand been inserted in a zone where no wear was detected (upstream of the throat 3 of the Venturi tube).

The probe II, of which a plan view of the exposed surface is shown in FIG. 8, comprised an insulating core 5 of epoxy resin incorporating a titanium working electrode 7 (grade 2) of cylindrical shape so as to present an exposed surface having the shape of a ring. This probe also included a first auxiliary electrode 9 constituted by type 316 stainless steel rod positioned at the center of the ring formed by the working electrode 7, and a second auxiliary electrode 11 constituted by a type 316 stainless steel cylinder mounted coaxially around the titanium working electrode 7.

The probes I and III had structures identical to the probe II except that they did not have the second auxiliary electrode 11 shown in FIG. 8.

In all cases, appropriate mounting means (threading through the wall 15 of the Venturi tube at selected locations) and adequately connected lead wires 19 have of course been used.

Figure 9:
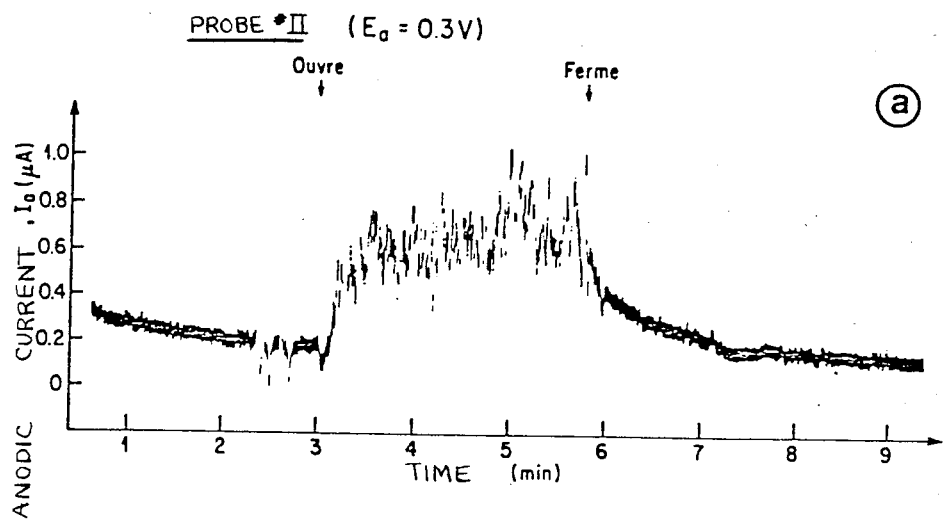
FIG. 9 is a curve giving the value of the anodic current measured as a function of time by one of the downstream probes on the pump illustrated in FIG. 6.
Figure 10:
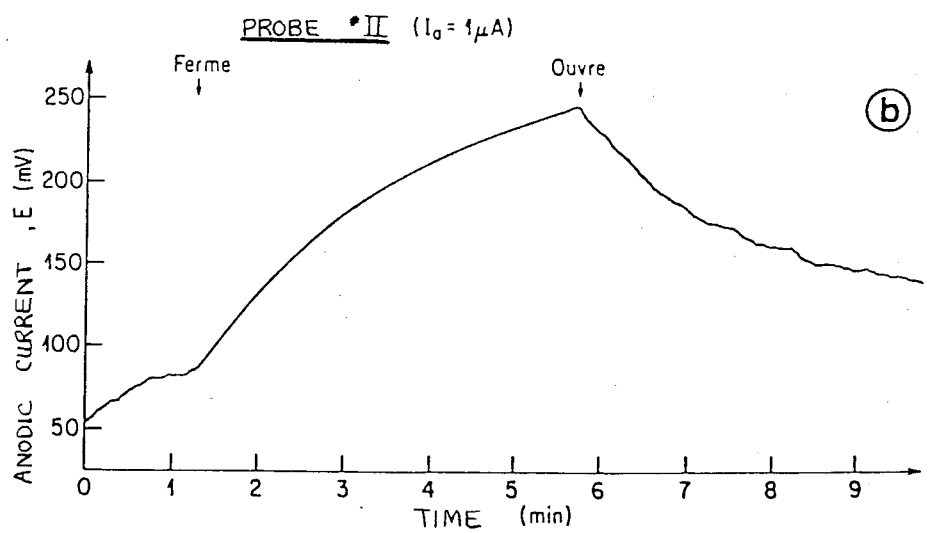
FIG. 10 is a curve giving the value of the anodic voltage measured by the probe used for the measurement plotted on FIG. 9.
Figure 11:
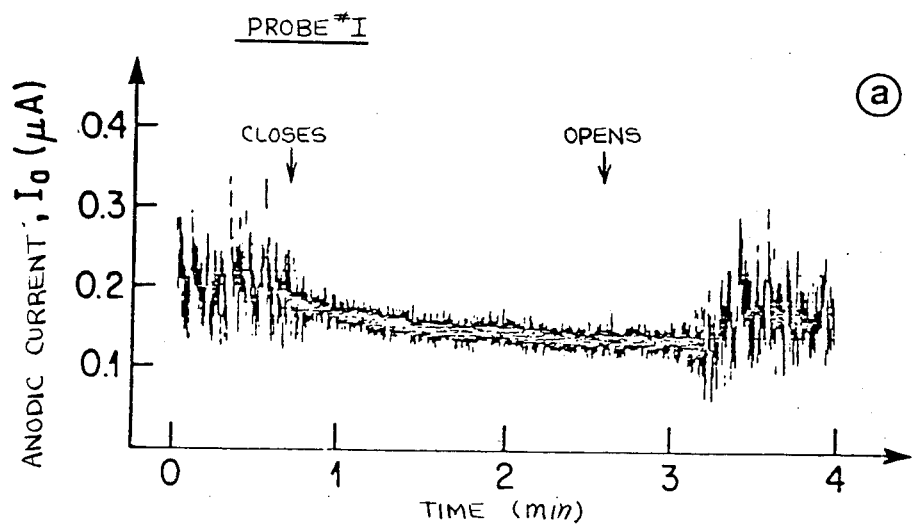
FIG. 11 is a curve giving the value of the anodic current measured by another probe provided upstream in the pump illustrated in FIG. 6.
Figure 12:
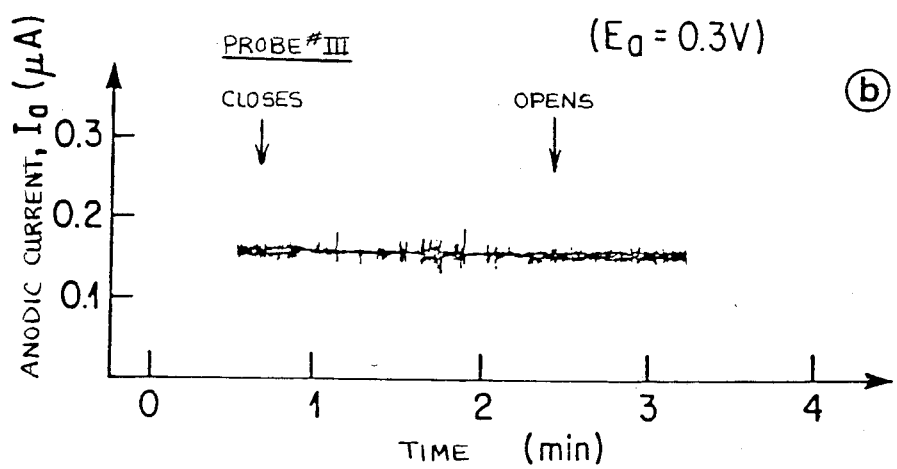
FIG. 12 is a curve giving the value of the anodic current measured by a third probe provided downstream in the pump illustrated in FIG. 6.

The measurements obtained with the probes I, II and III operating in potentio-static conditions (constant potential fixed at 0.3 volt relative to 316 stainless steel) are shown respectively on FIGS. 11, 12 and 9. The results obtained with the probe II in galvano-static conditions (constant applied current of 1 $\mu$A) appear on FIG. 10.

As can be observed, the probe II located in the strongest erosion zone, also shows the largest increase in anodic current when the high pressure water tap activating the pump has been opened. This measured increase in anodic current is 0.5 $\mu$A. Furthermore, FIG. 9 shows that—under potentio-static conditions, the response period of the probe and consequently of the complete detection system is extremely fast and that—it is additionally possible to note the current impulses that are characteristics of the uneven erosive cavitation that may besides be associated with the audible noise. FIG. 10 illustrates that, under galvano-static conditions, the same probe II measures a change in anodic voltage of more than 100 mV produced by the appearance or the disappearance of the erosive cavitation. It is noted however that with an applied anodic current of 1 $\mu$A, the repassivation time constant is rather long (in the order of 10 minutes) and the unevenness of the erosive cavitation is far less notable. The probe I has shown a signal of about 0.1 $\mu$A whereas no mean activation has been noted on probe III located in a no-cavitation area.

The calibration carried out at the same time in laboratory on an ultrasonic cavitation bench has shown that, with the probes used, an activation current of about 5 $\mu$A/cm$^2$ was obtained for an erosion rate of 1 mm per year of 316 stainless steel. According to this calibration, the probe II would thus give a localized erosion rate of 0.1 mm/year for the 316 steel, whereas the probe I would give a rate of 0.02 mm/year.

These results appear somewhat weak if they are compared to the observations made on a similar pump under full operation. This difference may however be explained by an increase in the diameter of the eroded particles and/or a decrease in the passivation charges under test conditions where water was quite pure.

The accuracy of the detector used in this test could therefore be improved by improving the laboratory calibration for very weak erosion rates in water conditions that are a bit closer to the conditions met in industry.

Nevertheless, this test illustrates the efficiency as well as the good operation of the method and of the device according to the present invention.

This test likewise shows that the measurement of anodic activation currents produced, by erosion of metallic particles, on passivated surfaces in aqueous solution constitutes an excellent means of quantitatively detecting the rate of cavitation erosion. Any wear in aqueous medium by erosion or abrasion without metal-metal contact may be detected with this technique.

Furthermore, the use of a metal such as titanium offers a reproducibility within a wide range of erosion rates going from 0.05 to 100 mm/year.

This technique may of course be used with adequate instrumentation for the development and supervision of hydraulic machines. This technique may therefore contribute to lower the costs and damages due to erosive cavitation.

EXAMPLE 2

A device according to the invention for detecting the activity of erosive cavitation has been tried on an ultrasonic cavitation bench in a laboratory to show and quantify the absorbing effect of air bubbles on the erosion rate at the surface of an electrode.

Figure 13:
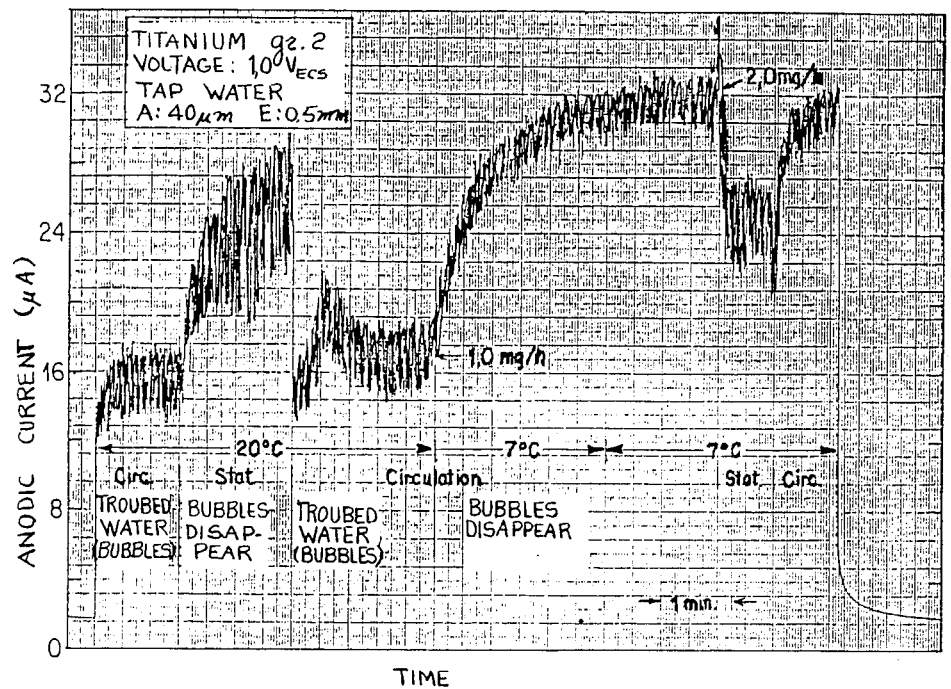
FIG. 13 is a curve giving the value of the anodic current (and of the erosion rate) obtained by ultrasonic cavitation in the presence of air bubbles in the liquid used.

The intensity of the anodic current measured on a titanium electrode (grade 2) under a constant potential of 1 volt SCE in a cavitation bench with a distance of 0.5 mm for a vibration amplitude of 40 $\mu$m is given in terms of time on the curve of FIG. 13 of the drawings. As may immediately be observed, the fact that the presence of bubbles directly affects the measurement clearly shows the efficiency of the device according to the invention for showing and quantifying the absorbing effect of air bubbles on the erosive cavitation in a hydraulic machine. This curve indeed shows the important absorbing effect of the air bubbles produced by using a mixture of pressurized hot and cold water which divides by two the rate of erosion for the same vibration amplitude.

Various modifications may of course be made to the method and device described above without departing from the scope of the present invention. Likewise, other applications may be envisaged such as, for example, the measure of any type of wear, erosion or abrasion, without metal-to-metal contact in aqueous medium (wear from sand in water; abrasion from a grinding wheel in water, etc. . . . ).

We claim:

1. Method of quantitatively and directly measuring the intensity of erosive cavitation present in an aqueous solution, said method comprising:

mounting, in said solution, a set of electrodes, comprising a reference electrode, at least one auxiliary electrode, and at least one working electrode made of a metal selected from metals capable of forming highly insulating oxide films becoming thicker by ionic mobility under the action of an electric field, the said at least one working electrode being located in a zone where cavitation is to be measured;

incubating the said at least one working electrode, prior or after its mounting, by subjecting it to mechanical cavitation for a period of time sufficient to obtain stabilization of the erosive cavitation phenomenon;

applying a constant anodic voltage onto said at least one working electrode after the incubation step, by means of said auxiliary and reference electrodes;

measuring the intensity of the anodic current; and detecting and measuring any variation in the said intensity of the current, each variation thus measured being directly related to the intensity of erosive cavitation in the said zone.

2. A method as claimed in claim 1, wherein said working electrode is made of a metal selected from the group constituted by magnesium, niobium, tantalum, titanium and zirconium.

3. A method as claimed in claim 2, wherein said constant anodic voltage applied across said working electrode is selected so that the measured variations in the intensity of the anodic current be directly proportional to the activity of erosive cavitation.

4. A method as claimed in claim 3, wherein said aqueous solution comprising water and wherein said working electrode is made of titanium and said constant anodic voltage applied across said working electrode is of the order of 0.5 V measured with respect to the reference electrode.

5. A method as claimed in claim 4, wherein said titanium is of a grade not greater than 2.

6. A method according to claim 5, wherein:
said titanium working electrode has an annular exposed surface, and
said auxiliary electrode is a stainless steel rod of the 316 type located centrally of said annular surface.

7. A method as claimed in claim 6, wherein said reference electrode is a satruated calomel electrode or a stable passive metal electrode.

8. A device for quantitatively and directly measuring the intensity of erosive cavitation present in an aqueous solution comprising:
a set of electrodes mounted in the said solution and comprising a reference electrode, at least one auxiliary electrode, and at least one working electrode made of a metal selected from those capable of forming highly insulating oxide films becoming thicker by ionic mobility under the action of an electric field, the said at least one working electrode being located in a zone or zones where cavitation is to be measured;
means for incubating the said at least one working electrode by subjecing it to mechanical cavitation for a period of time sufficient to obtain stabilization of the erosive cavitation phenomena:
means for measuring the intensity of the anodic current and to detect and measure any variation in the intensity of the said current after having previously incubated said at least one working electrode, each variation thus measured being directly related to the intensity of erosive cavitation in the measuring zone.

9. A device as claimed in claim 8, wherein each working electrode is made of metal selected from the group constituted by magnesium, niobium, tantalum, titanium and zirconium.

10. A device according to claim 9, wherein the constant anodic voltage applied across each working electrode is selected so that the measured variations in the intensity of the anodic current are directly proportional to the activity of erosive cavitation.

11. A device according to claim 10, wherein said liquid is water and wherein each working electrode is made of titanium and said constant anodic voltage applied across each working electrode is of the order of 0.5 V measured with respect to the reference electrode.

12. A device according to claim 11, wherein titanium is of a grade not greater than 2.

13. A device according to claim 11, wherein:
each titanium working electrode has an annular exposed surface;
each auxiliary electrode is a stainless steel rod of the 316 type located centrally of said annular surface formed by one of said working electrodes, and
said auxiliary electrode and said working electrode forming a probe mounted in one of the zones where cavitation is to be measured.

14. A device according to claim 13, used for the detection and the measurement of cavitation present at the surface of a part in contact with water, wherein each probe is inserted in the said part in such a way as to be flush with the surface thereof.

15. A device as claimed in claim 14, wherein said part is made of metal and constitutes said reference electrode, each probe being electrically insulated from said part.

16. A device as claimed in claim 15, comprising a plurality of probes and wherein the means for applying a constant anodic voltage across each of said working electrodes of said probes comprise a multiple high impedance potentiostat, the said potentiostat applying a constant anodic voltage separately across each of said working electrodes.

17. A device as claimed in claim 16, wherein the means for measuring the intensity of the anodic current comprise multi-scale galvanometers, each galvanometer measuring the intensity of the anodic current at one of said probes.

18. A device as claimed in claim 17, further comprising a multiplexer controlled by an electronic programmable device including a clock to adjust the frequency and the duration of each measurement.

19. A device as claimed in claim 18, further comprising a digital integrating voltmeter suitable to treat the signals provided by each of said galvanometers to improve the accuracy of the measuments.

20. A device as claimed in claim 19, wherein said programmable electronic device comprises a microcomputer or microprocessor and is provided with means to receive and store the signals provided by each probe.

21. A device as claimed in claim 20, wherein the said programmable electronic device is additionally provided with means for treating the stored signals to translate them into erosion rate units, loss of accumulated metal, penetration depth or operation period.

22. A device as claimed in claim 21, wherein the said programmable electronic device is further provided with means to illustrate the obtained results in analogue or digital form for a continuous display.

23. A device as claimed in claim 20, wherein the programmable electronic device is further provided with a digital outlet connected to a control system.

24. A device as claimed in claim 16, wherein the said reference electrode is in the form of a probe and of the same shape as each of the other probes.

25. A device as claimed in claim 11, wherein the surface of each titanium working electrode is initially tinted by anodization to allow a fine visual localization of the real cavitation zone.

26. A device as claimed in claim 11, wherein the working electrode is made up of the whole of a titanium hydraulic machine in which cavitation is to be controlled.

* * * * *